(12) United States Patent  
Fujita

(10) Patent No.: US 8,330,102 B2  
(45) Date of Patent: Dec. 11, 2012

(54) METHOD AND DEVICE FOR VISUALIZING DISTRIBUTION OF LOCAL ELECTRIC FIELD

(75) Inventor: Jun-ichi Fujita, Sakuragawa (JP)

(73) Assignee: Japan Science and Technology Agency, Saitama (JP)

( * ) Notice: Subject to any disclaimer, the term of this patent is extended or adjusted under 35 U.S.C. 154(b) by 231 days.

(21) Appl. No.: 12/921,991

(22) PCT Filed: Mar. 13, 2009

(86) PCT No.: PCT/JP2009/054901  
§ 371 (c)(1),  
(2), (4) Date: Nov. 30, 2010

(87) PCT Pub. No.: WO2009/113670  
PCT Pub. Date: Sep. 17, 2009

(65) Prior Publication Data  
US 2011/0068266 A1    Mar. 24, 2011

(30) Foreign Application Priority Data

Mar. 13, 2008    (JP) .................................. 2008-064682  
Mar. 26, 2008    (JP) .................................. 2008-081187

(51) Int. Cl.  
*H01J 37/26*    (2006.01)
(52) U.S. Cl. ....................................................... 250/307
(58) Field of Classification Search ................... 250/307  
See application file for complete search history.

(56) References Cited

OTHER PUBLICATIONS

Fujita et al., 'In-Site Visualization of Local Field Enhancement in an Ulta Sharp Tungsten Emitter under a Low Voltage Scanning Transmission Electron Microscope' Japanese Journal of Applied Physics, vol. 46, No. 20, 2007, pp. 498-501.*  
Fujita et al., 'Multilevel visualization of local electric field at probe apex using scanning electron microscopy' J. Vac. Sci. Tech. B, vol. 26, p. 2069, 2008.*

* cited by examiner

*Primary Examiner* — Jack Berman  
*Assistant Examiner* — Eliza Osenbaugh-Stewart  
(74) *Attorney, Agent, or Firm* — Wenderoth, Lind & Ponack, L.L.P.

(57) ABSTRACT

A method which visualizes the distribution of a local electric field formed near a sample 2 is disclosed. A primary electron beam 1 which passes through the local electric field formed near the sample 2 is deflected by the local electric field, secondary electrons which are generated and emitted from a detection element provided downstream of an orbit of the deflected primary electron beam 1 are detected by a secondary electron detector 6, and an image formed based on the detected signal and a scanning electron beam image obtained by scanning the sample 2 are synthesized thus visualizing the distribution of the local electric field in multiple tones. Due to such an operation, it is possible to provide a method for visualizing the distribution of a local electric field in which the distribution of a local electric field can be obtained in multiple tone and in real time by performing image scanning one time using a usual electron beam scanning optical system.

18 Claims, 12 Drawing Sheets

METHOD AND DEVICE FOR VISUALIZING DISTRIBUTION OF LOCAL ELECTRIC FIELD

TECHNICAL FIELD

The present invention relates to a method and a device for visualizing the distribution of a local electric field, and more particularly to a technique which can visualize the distribution of a local electric field formed near a sample in multiple tone and in real time using an electron beam scanning optical system.

BACKGROUND ART

The visualization of a local electric field has been expected to give an important clue in the evaluation of performances or functions or a trouble analysis of a solid device, a CNT (carbon nanotube) transistor, a light emitting element, an electron emission element which constitutes a nano structural body or, to be more specific, a trouble diagnosis analysis of an LSI or the evaluation of performances or functions or a trouble analysis of a defect of a gate portion or the like.

As a method for visualizing a local electric field whose importance is increasing in the development and the analysis of such a nano structural body, there has been proposed a local electric field visualizing method which uses a scanning transmission electron microscope (STEM) (non-patent document 1). FIG. 11 is a conceptual view of such a method. An anode is arranged to face a conductive probe having a pointed tip end in an opposed manner, and when a voltage is applied to the anode, an extremely strong local electric field is induced on the tip end of the probe. When the probe is electrically conductive, the whole probe has the same potential. When the probe is placed in an electric field, that is, even when a potential gradient is present in a space, it is necessary to set the same potential to the whole probe. Accordingly, an apparent charge is induced in the tip end of the probe so that the potential of the probe is adjusted such that the whole probe has the same potential. That is, due to this apparent charge, a local electric field which is an extremely strong electric field is formed in the vicinity of the tip end of the probe to which the potential is applied. When a primary electron beam of the scanning transmission electron microscope passes through this strong local electric field, an orbit of the primary electron beam is largely deflected. That is, the deflection of the orbit of the primary electron beam is considered as the scattering where an electron orbit is deflected due to a Coulomb force between a point charge induced on the tip end of the probe and the primary electron beam, that is, is considered as Rutherford scattering.

Accordingly, in a transmission image of the scanning transmission electron microscope, electron beams are scattered and are deflected from an electron beam detector (STEM detector) mounted on a lower portion of a casing so that a detection signal is not generated in a region where the scattering occurs, thereby a black region appears surrounding the distal end of the probe.

In the Rutherford scattering, an electron draws a hyperbolic orbit. An orbit from infinity approximates a point charge with a fixed distance b (impact parameter). Thereafter, the orbit is bent and deflected due to a Coulomb interactive force between the electron and the point charge. Here, the impact parameter b is expressed by a following formula.

$$b = \frac{1}{4\pi\varepsilon_0} \frac{z_1 e^2}{mv^2} \cot\frac{\theta}{2}$$

In the formula, e indicates an elementary charge, $z_1 e$ indicates an apparent point charge induced on a tip end of a probe, m indicates an electron mass, $\delta_0$ indicates a dielectric constant in vacuum, v indicates velocity of a primary electron beam, and θ indicates a scattering angle.

As a result of such scattering, the orbit of the primary electron beam is deflected to the outside of the electron beam detector so that the black shadow is formed. By extracting a completely black portion of an image, that is, a black portion of a level equal to brightness which imparts blackness of the probe or the electrode, a region subjected to the deflection to an extent that the scanning electron is completely displaced to the outside of the electron beam detector is specified. It is needless to say that contrast and brightness can be arbitrarily adjusted in the scanning transmission electron microscope, and it is a premise that a darkest portion of a bright field image is not saturated.

From a black region on the tip end of the probe observed when the distal end of the probe and the anode are arranged with a gap of 10 μm as shown in FIG. 12(a) and a potential of 258V is applied to the anode, brightness of a level equal to the brightness of the probe is extracted. As a result, a white circular region shown in FIG. 12(b) is formed. All primary electron beams incident within the circular region are displaced to the outside of the electron beam detector, and a radius 1.5 μm of circular region at this point of time becomes the impact parameter b. The scattering angle θ is determined based on a radius of the electron beam detector and a distance between the electron beam detector and the tip end of the probe, and an electric field E on a boundary of the circular region is expressed by a following formula.

$$E = \frac{mv^2}{eb}\tan\frac{\theta}{2}$$

The electron field E is expressed by a following formula when the primary electron beam of low acceleration outside the application of relativity theory is used.

$$E = \frac{2V}{b}\tan\frac{\theta}{2}$$

Here, V indicates an acceleration voltage of the primary electron beam.

A scattering angle can be obtained based on the use of such relationship formula due to the size of the black shadow which appears due to scattering of electrons so that the intensity of a local electric field at an edge of the shadow can be obtained.

Non-patent Document 1: J. Fujita et al. "In-situ Visualization of Local Field Enhancement in an Ultra Sharp Tungsten Emitter under a Low Voltage Scanning Transmission Electron Microscope" Jpn. J. Appl. Phys. 46 (2007) 498-501

DISCLOSURE OF INVENTION

Problems to be Solved by the Invention

With the use of the technique disclosed in non-patent document 1, it is possible to obtain the intensity of a local electric field on an outer periphery of the shadow based on a size of the black shadow which appears due to scattering of electrons.

However, the projected electric field region obtained by the method disclosed in non-patent document 1 is the single black shadow and hence, although the intensity of the local electric field on the outer periphery of the shadow can be obtained, it is difficult to obtain the distribution of the intensity of the electric field over the whole region at one time. Further, it may be possible to obtain the distribution of the intensity of the electric field over the whole region by collecting data amounting to plural sheets while changing the acceleration speed of the primary electron beam, in this case, it is difficult to visualize the change rapidly and in real time and hence, there is a room for improvement.

The present invention has been made under such circumstances, and it is an object of the present invention to provide a novel method and device for visualizing the distribution of a local electric field which can obtain the distribution of the local electric field whose importance is steadily increasing as a means for developing or evaluating a nano structural body, and as a means for performing a mechanical distortion analysis or an operation analysis dependent on a local electric field of a nano structural body, MEMS or the like by one image scanning in multiple tone and in real time.

Further, it is an another object of the present invention to provide a novel method and device for visualizing the distribution of a local electric field which can perform two-dimensional mapping of the distribution of the local electric field.
Means for Solving the Problems According to the present invention, to achieve the above-mentioned objects, firstly, there is provided a method for visualizing the distribution of a local electric field formed near a sample in an electron beam scanning optical system, wherein a primary electron beam which passes through the local electric field formed near the sample is deflected by the local electric field, secondary electrons which are generated and emitted from a detection element provided downstream of an orbit of the deflected primary electron beam are detected by a secondary electron detector, and an image formed based on the detected signal and a scanning electron beam image obtained by scanning the sample are synthesized thus visualizing the distribution of the local electric field in multiple tone.

Secondly, In the above-mentioned first invention, there is provided the method for visualizing the distribution of a local electric field, wherein the sample has a projecting portion, and the local electric field is formed near the projecting portion.

Thirdly, in the above-mentioned first or second invention, there is provided the method for visualizing the distribution of a local electric field, wherein a potential is applied to the sample.

Fourthly, in the above-mentioned any one of the first to third inventions, there is provided the method for visualizing the distribution of a local electric field, wherein a detection element having the grid structure which is constituted of a plurality of linear portions arranged in a spaced apart manner at a fixed interval is used as the detection element.

Fifthly, in the above-mentioned fourth invention, there is provided the method for visualizing the distribution of a local electric field, wherein a detection element in which two sets of grid structures each of which is constituted of a plurality of linear portions are arranged orthogonal to each other is used as the detection element.

Sixthly, in the above-mentioned fourth or fifth invention, there is provided the method for visualizing the distribution of a local electric field, wherein a detection element in which a grid is formed on a substrate, the grid is constituted of a metal element, and a constitutional element of the grid and a constitutional element of the substrate differ from each other in secondary electron generation efficiency with respect to a bombardment of a primary electron beam is used as the detection element.

Seventhly, in the above-mentioned sixth invention, there is provided the method for visualizing the distribution of a local electric field, wherein the detection element in which the grid is constituted of Al, Cu or Au is used.

Eighthly, in the above-mentioned sixth or seventh invention, there is provided the method for visualizing the distribution of a local electric field, wherein a bias voltage is applied to the grid.

Ninthly, in the above-mentioned eighth invention, there is provided the method for visualizing the distribution of a local electric field, wherein a contrast of an image which indicates the distribution of the local electric field is adjusted by adjusting intensity of the bias voltage applied to the grid.

Tenthly, in any one of the above-mentioned second to ninth inventions, there is provided the method for visualizing the distribution of a local electric field, wherein grid lines which constitute the detection element are individually connected to a register, and a scattering angle of the primary electron beam based on the local electric field is detected based on a signal from the register.

Eleventhly, there is provided a method for evaluating a local electric field distribution characteristic, wherein a distribution characteristic of a local electric field of the sample is evaluated using the method for visualizing the distribution of a local electric field described in any one of the above mentioned first to tenth inventions. Further, twelfthly, there is provided the method for evaluating a local electric field distribution characteristic, wherein the dependency of a mechanical distortion or an operation of the sample on the local electric field is evaluated.

Further, thirteenthly, there is provided a local electric field distribution visualizing device which enables the visualization of the distribution of a local electric field formed near a sample in an electron beam scanning optical system in multiple tones, the local electric field distribution visualizing device including at least: (a) a scanning radiation part which radiates a primary electron beam to the sample; (b) a detection part which detects the primary electron beam; (c) a detection element part which detects the primary electron beam deflected by a local electric field formed on the sample; (d) a secondary electron detection part which detects secondary electrons generated and emitted from the detection part which detects the primary electron beam; (e) an image conversion part which converts a signal from the secondary electron detection part; (f) an image conversion part which converts a signal from the primary electron beam detection part; and (g) an image synthesizing and displaying part which synthesizes and displays images from the image conversion parts (e), (f).

Fourteenthly, there is provided the local electric field distribution visualizing device, wherein the sample has a projecting portion, and the local electric field is formed near the projecting portion. Fifteenthly, there is provided the local electric field distribution visualizing device, wherein a potential applying part which applies a potential to the sample is provided. Sixteenthly, there is provided the local electric field distribution visualizing device, wherein the detection element part (c) includes a detection element having the grid structure which is constituted of a plurality of linear portions arranged in a spaced apart manner at a fixed interval. Seventeenthly, there is provided the local electric field distribution visualizing device, wherein the detection element part (c) includes a detection element in which two sets of grid structures each of which is constituted of a plurality of linear portions are arranged orthogonal to each other. Eighteenthly, there is provided the local electric field distribution visualizing device, wherein the device includes a grid bias voltage applying part which applies a bias voltage to the grid.

Here, in this specification, a nano structural body and an electronic device structural body which are subject to evaluation or analysis are collectively referred to as a sample.

EFFECTS OF THE INVENTION

According to the invention of claim 1, an image of the distribution of the local electric field which is formed near the sample when a potential is applied to the sample such as a nano structural body or an electronic device structural body including a nano gap device such as an R-RAM (resistive RAM) can be visualized in multiple tone by synthesizing the image of the distribution of the local electric field in an SEM image and, further, a change of the image of the distribution of the local electric field can be traced in real time. Accordingly, the fine or minute structure and shape of the sample such as the nano structural body or the electronic device structural body at a nano-scale, and the characteristics, the properties and functions of the particular distribution of the local electric field derived from the constitution of element and a change thereof can be grasped in real time and hence, the visualized information obtained by the present invention makes the extremely important contribution to the development and analysis of the nano structural body.

According to the inventions of claims 2 to 8, a large quantity of secondary electrons are generated and emitted due to the bombardment of the deflected primary electron beam on the grid so that an image having the distribution of the local electric field with a favorable S/N ratio can be obtained. That is, this advantageous effect can be further enhanced by providing the projecting portion to the sample and by forming the local electric field near the projecting portion (claim 2), by applying the potential to the sample (claim 3), by using the detection element having grid structures each of which is constituted of a plurality of linear portions arranged in a spaced-apart manner at a fixed interval (claim 4), by using the detection element in which two sets of grid structures each of which is constituted of a plurality of linear portions are arranged orthogonal to each other (claim 5), by using the detection element in which the grid is formed on the substrate, the grid is constituted of the metal element, and the constitutional element of the grid and the constitutional element of the substrate differ from each other in secondary electron generation efficiency with respect to a bombardment of the primary electron beam (claim 6), by using the detection element in which the grid is constituted of Al, Cu or Au (claim 7), or by applying a bias voltage to the grid (claim 8). Further, two-dimensional mapping of the distribution of the local electric field can be realized (claim 5).

According to the invention of claim 9, a secondary electron generation quantity can be controlled by adjusting intensity of the bias voltage applied to the grid and hence, a contrast of an image which indicates the distribution of the local electric field can be adjusted whereby it is possible to realize a flexible change of intensity of a contour image but also the negative/positive inversion of image.

According to the invention of claim 10, the grid lines are individually connected to the ND converter means, and the impingement of the primary electron beam is detected as the digital data and hence, the deflection angle of the primary electron beam can be detected as positional information in real time thus realizing the high-speed data analysis.

According to the inventions of claim 11 and claim 12, the local electric field distribution characteristics intrinsic to the sample can be evaluated by the above-mentioned method.

Further, according to the inventions of claims 13 to 18, it is possible to provide the device which can carry out the above-mentioned visualizing method.

BEST MODE FOR CARRYING OUT THE INVENTION

Figure 1:
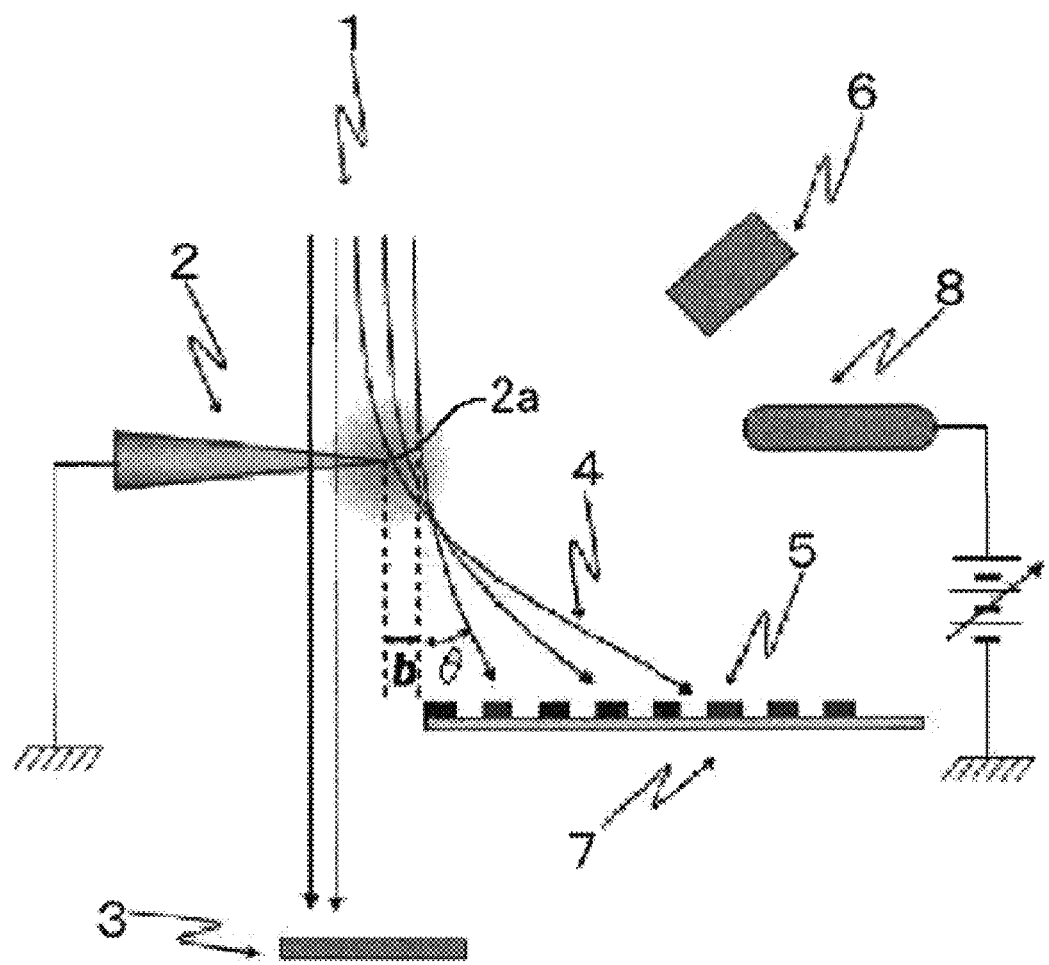
FIG. 1 is a schematic view showing a method for visualizing the distribution of a local electric field according to a first embodiment of the present invention.

A method for visualizing the distribution of a local electric field according to the present invention is explained in detail hereinafter.

The method for visualizing the distribution of a local electric field of the present invention is, for example, in a representative example, exemplified as a method which visualizes the distribution of a local electric field formed near a sample using a scanning electron microscope optical system. A primary electron beam which passes through the local electric field formed near the sample is deflected by the local electric field, secondary electrons which are generated and emitted from a detection element provided downstream of an orbit of the deflected primary electron beam are detected by a secondary electron detector, and an image formed based on the detected signal and an SEM image obtained by scanning the sample are synthesized thus visualizing the distribution of the local electric field in multiple tone.

As a device or a system which enables such visualization, there is provided, as described previously, a local electric field distribution visualizing device which enables the visualization of the distribution of a local electric field formed near a sample in an electron beam scanning optical system in multiple tone, wherein the local electric field distribution visualizing device includes at least: (a) a scanning radiation part which irradiates a primary electron beam to the sample; (b) a detection part which detects the primary electron beam; (c) a detection element part which detects the primary electron beam deflected by a local electric field formed on the sample; (d) a secondary electron detection part which detects secondary electrons generated and emitted from the detection part which detects the primary electron beam; (e) an image conversion part which converts a signal from the secondary electron detection part; (f) an image conversion part which converts a signal from the primary electron beam detection part; and (g) an image synthesizing and displaying part which synthesizes and displays images from the image conversion parts (e), (f).

In the present invention, the sample may be an electric conductor or may be a material which is not conductive but can induce a local electric field when the material possesses a potential. Further, the sample which is subject to evaluation or analysis may be a sample which has a projecting portion or a sample which is formed into various configurations such as filaments provided that the sample has a portion which is formed into a shape capable of inducing a local electric field near the sample on at least a part of the sample. Further, the evaluation or analysis in the present invention may be carried out in a state where the sample constitutes a cathode and an anode is arranged to face the sample in an opposed manner or may be carried out with respect to the sample which is in an operative state and a potential is applied to a portion of the sample which induces a local electric field near the sample.

For example, in the scanning electron microscope (SEM), the primary electron beam is scanned using a deflection signal in the vertical direction and a deflection signal in the horizontal direction in the same manner as a usual TV image. An SEM image (scanning electron microscope image) is formed such that the image is farmed by synchronizing the intensity of a generated secondary electron beams with vertical and horizontal signals at a scanning position on the sample, and the configuration of a surface of the sample is outputted as an image.

In the scanning electron microscope optical system, assuming that a potential is applied to a conductive sample, when the conductive sample includes a projecting portion which has a pointed tip end, a local electric field is formed near the tip end of the projecting portion. When a primary electron beam passes through the local electric field, a Coulomb force acts and an electron orbit is deflected due to Rutherford scattering. A detection element is provided downstream of the deflected electron orbit, and the primary electron beam is irradiated to the detection element so as to make the detection element generate and emit secondary electron beams.

As the detection element, a detection element which has the grid structure is preferably used. In this case, as the detection element, a detection element which has the grid structure constituted of a plurality of linear portions arranged in a spaced-apart manner at a fixed interval is preferably used. Each grid line may have a width of approximately 0.5 to 3 μm and a thickness of approximately 0.05 to 0.2 μm, for example. A line distance may be set to approximately 5 to 20 μm, and the number of grid lines may be set to approximately 1 to 10. Further, a distance in the horizontal direction between the detection element and the tip end of the projecting portion may be set to approximately 50 mm and a distance in the vertical direction between the detection element and the distal end of the projecting portion may be set to approximately 30 mm. It is needless to say that these values are given only as examples and are varied depending on an acceleration voltage applied to an electron beam, the intensity of a local electric field to be detected, and the degree of resolution. Although the detection element may have the structure where these grid lines are formed on a substrate, as a material for forming the grid, it is preferable to use a metal material for allowing the grid to emit a large quantity of secondary electrons. Al, Cu and Au are exemplified as a particularly preferable constitutional material. To obtain a clear distribution image, it is preferable that the constitutional element of the grid and the constitutional element of the substrate differ from each other in secondary electron generation efficiency with respect to the bombardment of the primary electron beam. When the difference between an atomic weight of the constitutional element of the grid and an atomic weight of the constitutional element of the substrate is large, the difference in secondary electron generation efficiency between these constitutional elements becomes large. As a typical example of a material for forming the substrate, silicon may be named. However, the material for forming the substrate is not limited to silicon.

Further, secondary mapping of the distribution of a local electric field becomes possible by arranging two sets of grid structures each of which is formed of a plurality of linear portions longitudinally and laterally, for example.

When the deflected primary electron beam collides with the detection element, a large quantity of secondary electrons are generated and emitted and hence, the secondary electrons are detected by a secondary beam detector, that is, a usual scintillator for an SEM image, for example. Then, an image formed based on the detected signal is synthesized with the SEM image obtained by scanning the sample so that the distribution of local electric field intensity can be visualized in multiple tone. That is, it is possible to obtain a contour image which reflects the local electric field intensity.

Here, by applying a bias voltage to the grid of the detection element, a generation quantity of the secondary electrons can be controlled and hence, it is possible to realize not only the adjustment of intensity of the contour image but also the negative/positive inversion.

Further, by connecting the individual grid lines to the A/D conversion means such as registers respectively and by detecting the collision of the primary electron beam as digital data, a deflection angle of the primary electron beam can be detected as positional information in real time, and it is also possible to obtain the distribution of local electric field intensity as digital data in real time by combining the deflection angle with a deflection control signal of the SEM.

To exemplify a typical example, when the tip-end electric field intensity is 1 MeV/m with respect to the primary electron beam of 5 keV, a scattering angle is approximately 20 mRad. Accordingly, when the grid is arranged away from the sample with a distance of 30 mm, it is possible to obtain the distribution of local electric field intensity with favorable SN using the grid having a pitch of approximately 10 µm.

For example, using the above-mentioned method and device, the present invention provides a method for evaluating a local electric field distribution characteristic in which a distribution characteristic of a local electric field of the sample is evaluated or a method for evaluating a local electric field distribution characteristic in which dependency of mechanical distortion or an operation of the sample on a local electric field is evaluated.

In view of the above, embodiments of the present invention are explained in more detail hereinafter.

(First Embodiment)

Next, the first embodiment of the present invention is explained in detail in conjunction with drawings.

As shown in FIG. 1, in a sample chamber of the scanning electron microscope, a primary electron beam 1 is focused by an objective lens (not shown in the drawing) and scans a surface of a conductive sample 2. An acceleration voltage of the primary electron beam 1 used in this embodiment is 5 keV. When a positive bias voltage is applied to an anode 8 which is arranged to face the grounded conductive sample 2 in an opposed manner, a potential gradient, that is, an electric field is formed between the conductive sample 2 and the anode 8. On a projecting portion (a local projecting portion formed on a tip end of a probe or the like) 2a having a pointed tip end of the conductive sample 2 arranged in the potential gradient, an apparent charge is formed on the distal end of the projecting portion 2a such that the potential becomes equal over the whole conductor, and an extremely strong local electric field is formed near the projecting portion 2a. When the primary electron beam 1 passes through the local electric field, Rutherford scattering is generated due to a Coulomb repulsive force so that the primary electron beam 1 is deflected. A distance from the distal end of the projecting portion 2a to the primary electron beam 1 is an impact parameter b. A deflection angle of the scattered primary electron beam 4(1) is indicated by θ.

A detection element having a grid 5 is arranged downstream of an orbit of the deflected primary electron beam 4(1), and the deflected primary electron beam 4(1) impinges on the grid 5. In this embodiment, the grid 5 is formed by arranging gold grid lines having a thickness of 100 nm and a width of 3 µm on a silicon oxide substrate 7 in a spaced-apart manner at a fixed interval of 10 µm pitch. Gold which is an element constituting the grid 5 and silicon which is an element constituting the substrate 7 largely differ from each other in an atomic weight and hence, the generation efficiency of the secondary electrons with respect to the primary electron beam radiation largely differs between gold and silicon. That is, when the primary electron beam 4(1) collides with the detection element, a large quantity of secondary electrons are emitted from the gold grid 5, while the secondary electrons emitted from the silicon substrate 7 are small.

Here, a method for manufacturing a detection element which includes the grid 5 is explained. A titanium film having a thickness of 5 nm is formed on the silicon oxide substrate 7 as an adhesive layer by vapor deposition and, subsequently, a gold film having a thickness of 100 nm is formed on the titanium film by vapor deposition. An NEB resist (negative electron beam resist) having a thickness of approximately 200 nm is formed on the gold film by coating, and a grid pattern is transferred to the resist by the electron beam exposure. Next, the substrate is loaded into an ion etching device, and the substrate is subject to milling using Ar ions of approximately 700 eV, 1 mA/cm$^2$.

Due to such treatment, the grid pattern is transferred to a Ti/Au film so that the detection element provided with the grid 5 is manufactured.

When a position of the scanned primary electron beam 1 is extremely near the tip end of the projecting portion 2a, the scattering angle of the primary electron beam 1 is increased and the primary electron beam 1 reaches the remotest grid 5 portion. On the other hand, the deflection angle of the primary electron beam 4(1) which passes a position away from the projecting portion 2a is small so that the primary electron beam 4(1) reaches the closest grid 5 portion. During such scanning, the position b through which the primary electron beam 1 passes is changed along with the electron beam scanning. For example, when the scanning is performed from a right side to a left side in the drawing, firstly, the primary electron beam 4(1) does not reach the grid 5 and hence, a peripheral space is visualized as a dark field of view in the vicinity of the tip end of the projecting portion 2a. On the other hand, when the primary electron beam 1 approaches the projecting portion 2a at a fixed distance from the projecting portion 2a, the primary electron beam 1 receives a Coulomb repulsive force and reaches the grid 5 at a left edge. An outermost portion of the projecting portion 2a in the SEM image at this stage is given brightness information by the secondary electrons from the grid 5 and is visualized as a white pixel. When the primary electron beam 1 further approaches the projecting portion 2a, although the primary electron beam 4(1) reaches the silicon substrate 7, a emission quantity of the secondary electrons from the silicon substrate 7 is small so that an image is visualized with black pixels. Hereinafter, along with the increase of the scattering angle of the primary electron beam 4(1) corresponding to the electric field intensity of the tip end of the projecting portion 2a, the arrival of the primary electron beam 1 to the grid 5 position and the arrival of the primary electron beam 1 to the silicon substrate 7 position are alternately repeated so that the distribution of the local electric field having white and black contours appears in an SEM image at a position corresponding to the tip end of the projecting portion.

Figure 2:
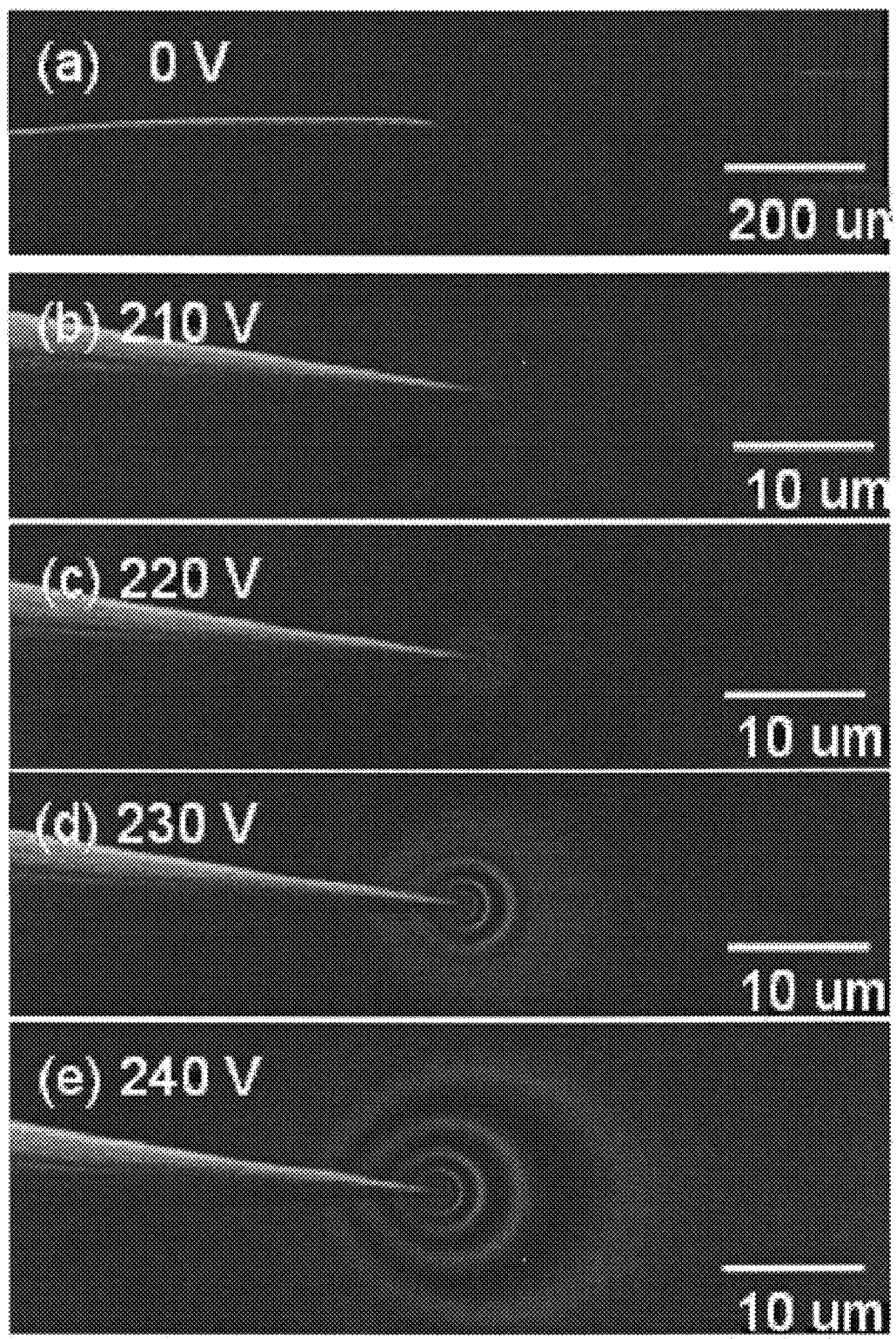
FIG. 2 is a schematic view showing a state in which the actual distribution of a local electric field according to the first embodiment of the present invention is visualized.

FIG. 2 shows a mode in which a local electric field is actually visualized using a photograph. FIG. 2(a) indicates a state where a potential of an anode 8 is 0V, and a shadow does not appear at a position of an image corresponding to the tip end of the projecting portion 2a. A horizontal distance between an outermost portion of the tip end portion 2a and the anode 8 is 500 µm. An object which is observed on a right end in FIG. 2(a) is a detection grid. By elevating a bias voltage to 210V in FIG. 2(b), 220V in FIG. 2(c), 230V in FIG. 2(d) and 240V in FIG. 2(e) in this order, a size of the ring which appears on the tip end of the projecting portion 2a is increased and the number of inner rings is also increased corresponding to the elevation of the bias voltage.

Figure 3:
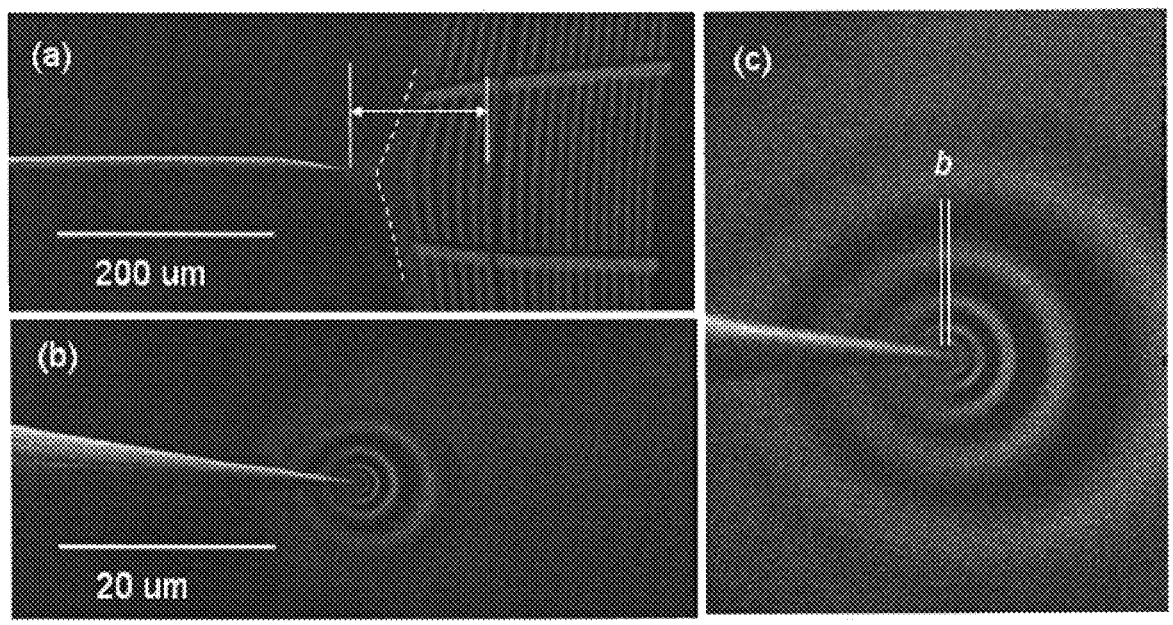
FIG. 3 is a schematic view showing a method for analyzing the distribution of the local electric field according to the first embodiment of the present invention.

Here, to analyze the state shown in FIG. 2(e) in more detail, it is understood that a gray region on an outermost periphery of the ring corresponds to an edge portion of the detection element. FIG. 3(a) shows the whole constitution in a reduced manner such that the positional relationship between the projecting portion 2a of the conductive sample 2 and the grid 5 can be understood more easily, FIG. 3(b) is a view corresponding to FIG. 2(e), and FIG. 3(c) shows the rings in an enlarged manner. Although the secondary electron emission intensity at a flat portion of the silicon substrate 7 is low, an edge portion of the grid 5 has a vertical edge surface and hence, the secondary electron emission intensity is specifically increased. This is the reason why concaves and convexes of the sample can be favorably observed using an SEM image. Since the secondary electron emission efficiency at the edge portion of the detection element is high, an outermost periphery of the ring is formed into a gray region having a large width. The largest ring near the tip end of the projecting portion 2a is a white ring shown in FIG. 3(c) which is an enlarged view. A radius of the ring is approximately 250 nm, and the radius of this innermost white ring corresponds to the impact parameter b. Further, it is understood that the innermost ring corresponds to the sixth grid line shown in FIG. 3(a) and the primary electron beam scattered at a position corresponding to the circumference of the ring near the tip end of the projecting portion 2a reaches the sixth grid line. That is, the primary electron beam is scattered in the horizontal direction toward the detection element having the grid 5 in the axial direction of the conductive sample 2 by 130 μm. To take a condition that the vertical distance from the projecting portion 2a to the grid 5 is 30 mm into consideration, the scattering angle θ becomes 0.0043 radian. Since the acceleration voltage of the primary electron beam 1 is 5 kV, the local electric field intensity on the innermost ring near the distal end of the projecting portion 2a can be calculated such that $E=V\theta \cong 87V/\mu m$.

The reason that an image of the grid 5 shown in FIG. 3(a) is formed into a curved state is that an electric field generated between the anode 8 and a cathode (projecting portion 2a) is constituted of two kinds of electric fields. One electric field is an electric field which is also referred to as an average electric field between the anode and the cathode and the other electric field is a local electric field which is formed on the tip end (projecting portion 2a) of the cathode. When a voltage is applied to the anode 8, the primary electron beam 1 is bent toward the anode 8 side due to such an average electric field and hence, eventually, the grid 5 approaches the tip end of the cathode in the SEM image whereby it appears that a distance between the tip end of the cathode and the grid 5 is narrowed. When a higher voltage is applied to the anode 8, since a grid potential is a ground potential in the same manner as the tip end of the cathode, another electric field is formed around the grid 5. Due to the average electric field around the grid 5, the image of the grid in the SEM image appears in a curved shape. However, even with such a curved grid shape, when the primary electron beam 4(1) scattered by the tip end (projecting portion 2a) of the cathode collides with a portion of the grid corresponding to a curved outermost peripheral portion of the grid image, by obtaining a scattering angle based on a distance between the visualized ring and the curved grid image using a Rutherford scattering formula, it is possible to obtain an accurate local electric field near the tip end (projecting portion 2a) of the cathode.

However, these contour-shaped rings are not formed by connecting absolute values of electric field intensities on respective coordinates. The primary electron beam 4(1) scattered by Rutherford scattering is detected by the grid 5 arranged in the direction of the anode 8 and hence, a scattering force in the horizontal direction toward the grid 5 is detected. That is, a direction cosine of an absolute value of the electric field in the grid direction is observed.

Figure 4:
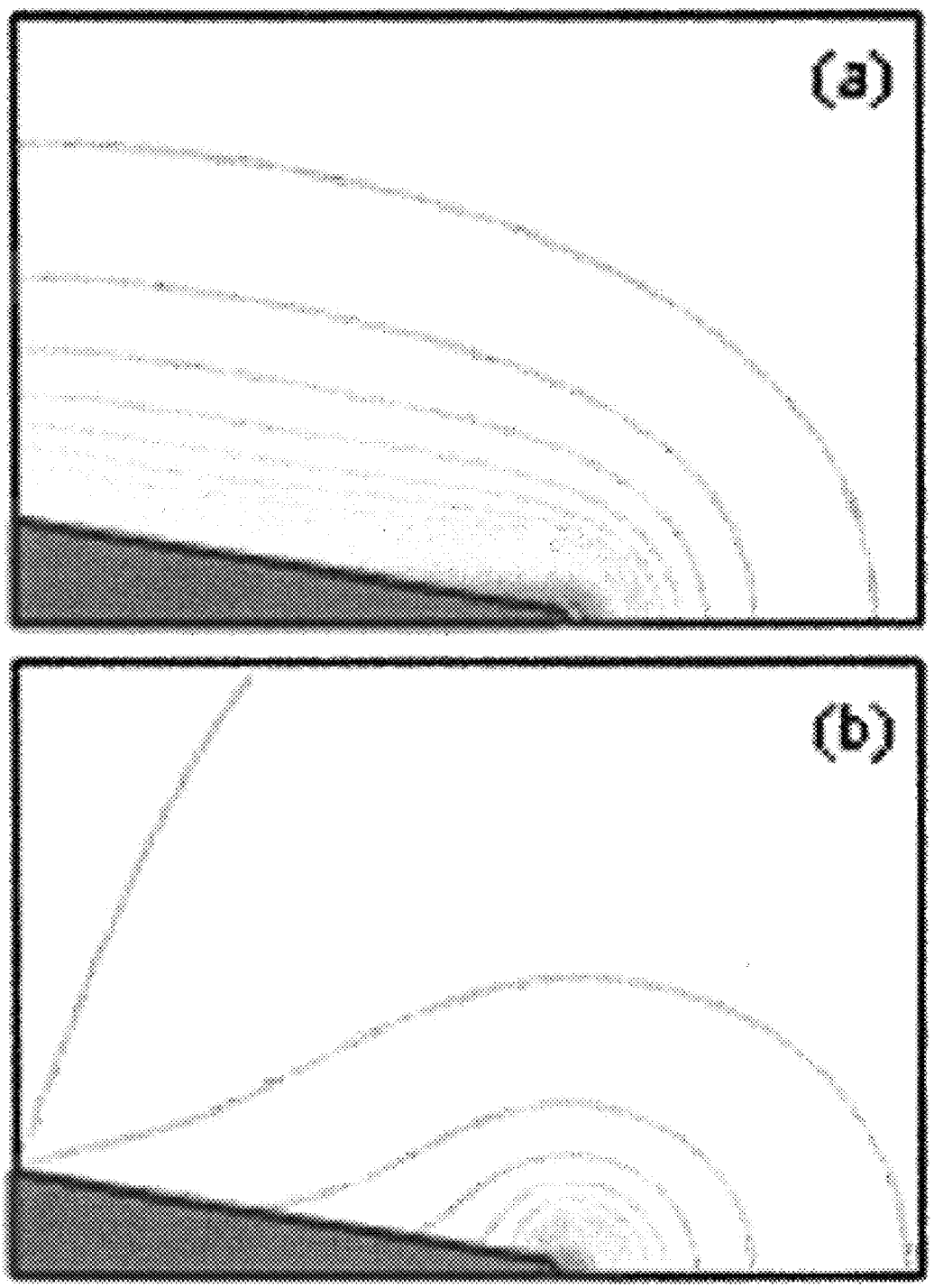
FIG. 4 is a schematic view showing the distribution of a local electric field according to the first embodiment of the present invention by a finite element method.

FIG. 4(a) shows a result of the electric field intensity near the tip end of the projecting portion 2a obtained by simulation using a finite element method (FEM). Since the conductive sample 2 is metal, the potential distribution has a gradient in the normal direction of a surface in accordance with the Gauss theorem. Accordingly, it is understood that an electric field is formed parallel to the surface by reflecting a shape of the projecting portion 2a. On the other hand, when a contour chart is drawn by sampling a cosine component of the electric field in the grid direction in FIG. 4(a) or in the right hand direction in the case shown in the drawing, a contour chart shown in FIG. 4(b) is obtained. It is understood that the contour chart favorably agrees with the ring-shaped electric field intensity distribution obtained by the method of the present invention.

That is, the electric field distribution obtained based on an output of the detection element having the grid 5 implies the observation of direction cosine component of the true electric field distribution in the detection element direction. That is, the true electric field distribution is obtained by converting the electric field intensity shown in FIG. 4(b) which shows the obtained direction cosine data to the electric field intensity shown in FIG. 4(a).

(Second Embodiment)

Next, the second embodiment of the present invention is explained in detail.

Figure 5:
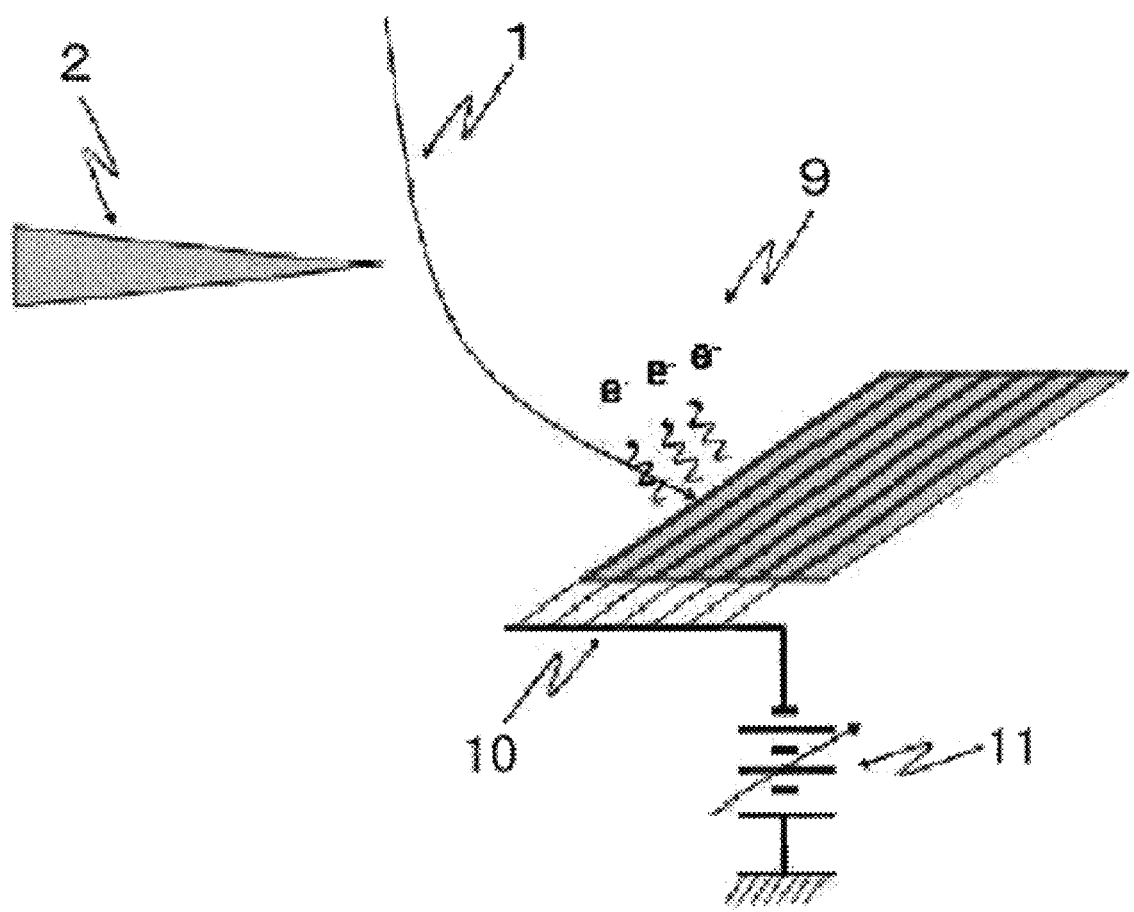
FIG. 5 is a schematic view showing a method for visualizing the distribution of a local electric field according to a second embodiment of the present invention.

In the above-mentioned first embodiment, the explanation has been made with respect to the case where the local electric field distribution can be visualized in the SEM image using the emission of secondary electrons from the grid 5. The adjustment of contrast in such visualization can be realized by applying a voltage to the grid 5. As shown in FIG. 5, by connecting the grid 5 and a bias power source 11 with each other using a bias line 10 so as to apply a minus or plus voltage to the grid 5, the emission intensity of secondary electrons can be suppressed or increased thus controlling the contrast of the distribution of a local electric field in an SEM image.

(Third Embodiment)

Figure 6:
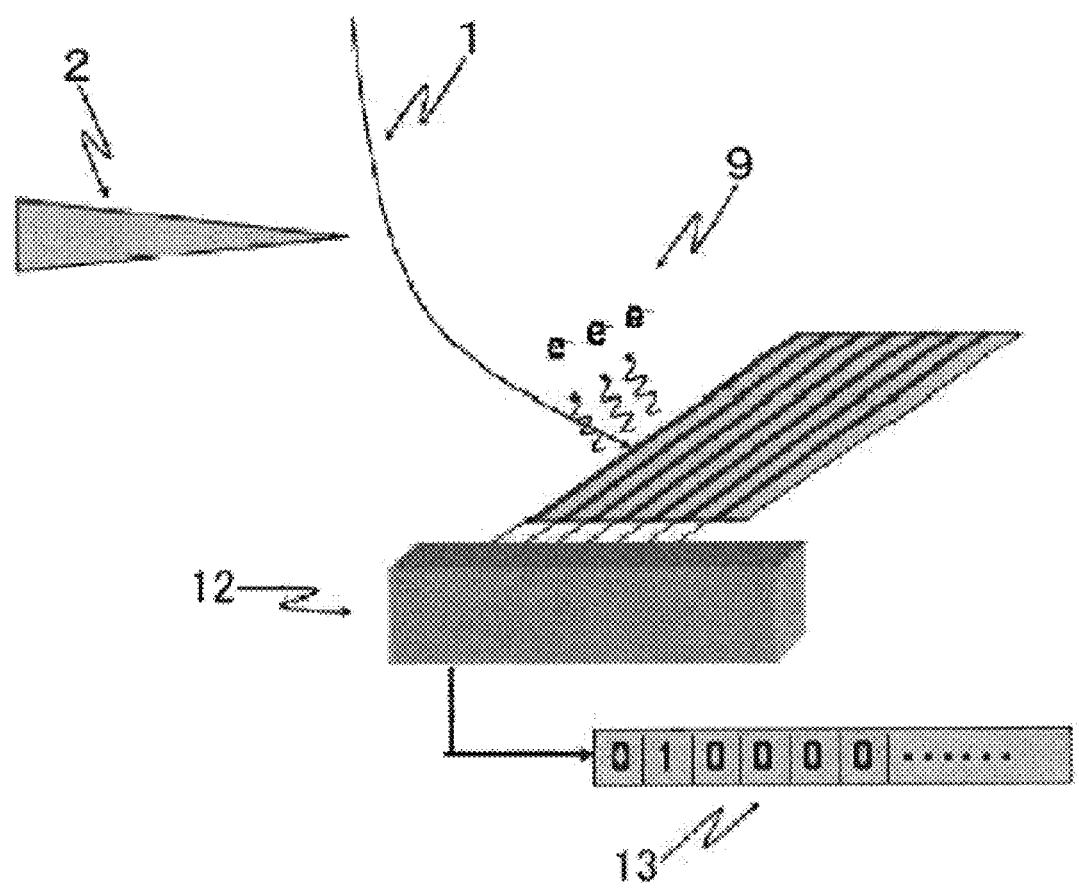
FIG. 6 is a schematic view showing a method for visualizing the distribution of a local electric field according to a third embodiment of the present invention.

Next, the third embodiment of the present invention is explained in detail in conjunction with FIG. 6.

When a primary electron beam 4(1) collides with each grid line of a grid 5, a probe current flows corresponding to a quantity of the incident primary electron beam 1 and a quantity of emitted secondary electron beams 9 and hence, a voltage of the grid line is changed. Here, a probe current differs in polarity depending on a bias voltage applied to the grid line. This voltage change is detected by a voltage detector 12, and grid position information is fetched as a bit data row by an A/D conversion means such as a shift register 13 and hence, it is possible to obtain the arrival position information of the primary electron beam 1 directly. That is, it is possible to fetch a deflection angle θ of the primary electron beam 4(1) due to the local electric field in real time corresponding to the scanning position information of the primary electron beam 1. Accordingly, it is possible to acquire, in real time, a 1 frame of a scanning electron microscope image as well as scattering angle information for 1 frame without requiring an image analysis.

(Fourth Embodiment)

Further, the fourth embodiment of the present invention is explained in detail in conjunction with FIG. 7 to FIG. 10.

In FIG. 1, the plurality of grids 5 are arranged at a fixed interval in the direction orthogonal to the direction that the anode 8 and the projecting portion 2a of the conductive sample 2 make. However, in an example shown in FIG. 7, a plurality of grids 5 are arranged at a fixed interval parallel to the direction which an anode 8 and a projecting portion 2a of a conductive sample 2 make.

Figure 7:
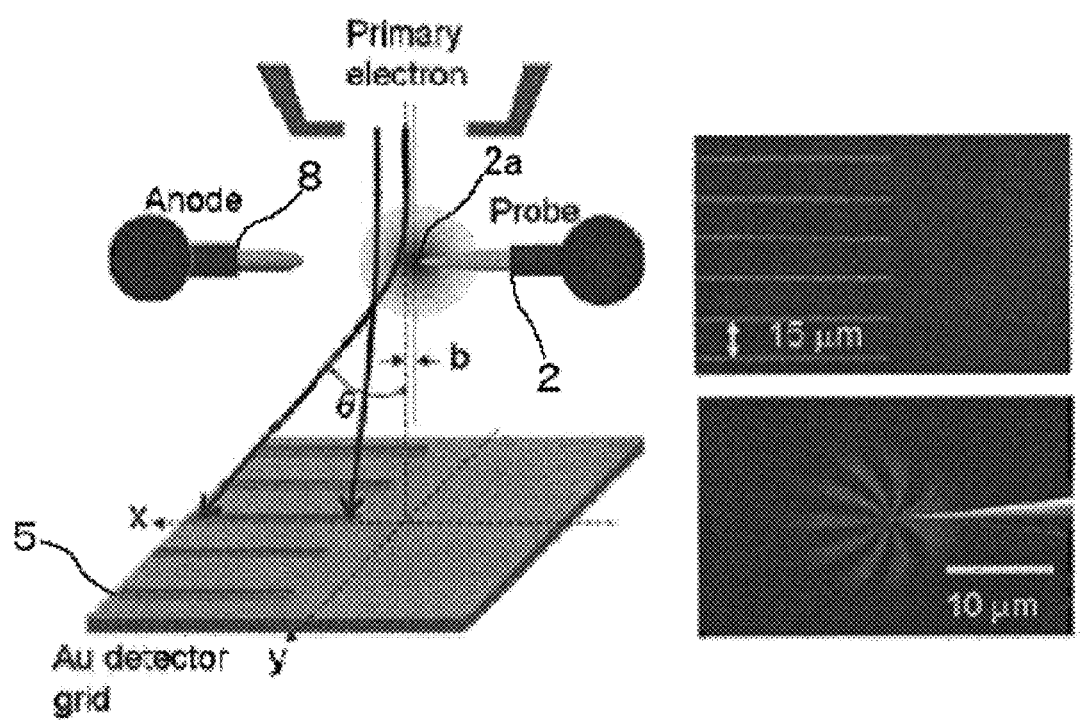
FIG. 7 is a schematic explanatory view showing a method for visualizing the distribution of a local electric field according to a fourth embodiment of the present invention, wherein a plurality of grids are arranged parallel to the direction which the plurality of cathodes and anodes make, and a schematic view showing a state where an actual distribution of local electric field is visualized by the method.

In the case shown in FIG. 1, the ring-shaped shadows are concentrically formed corresponding to the plurality of grids 5 (FIG. 2). However, when the grids 5 are arranged as shown in FIG. 7, as shown in a right lower view in FIG. 7, shadows corresponding to the plurality of grids 5 are formed into a radially extending spoke shape from a portion corresponding to the projecting portion 2a of the conductive sample 2. It is regarded that the same radially extending spoke portion has the same electric field component in the y direction.

Figure 8:
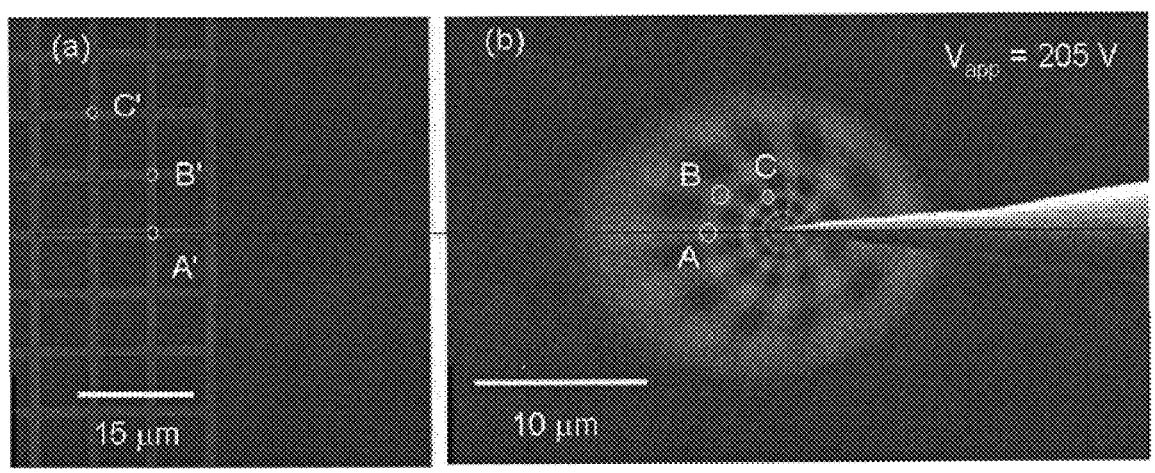
FIG. 8 is a schematic view in which a plurality of grid rows are arranged longitudinally and laterally in a grid array and also is a schematic view showing a state in which the actual distribution of the local electric field obtained by making use of the arrangement is visualized and two-dimensional mapping is performed according to a fourth embodiment of the present invention.
Figure 9:
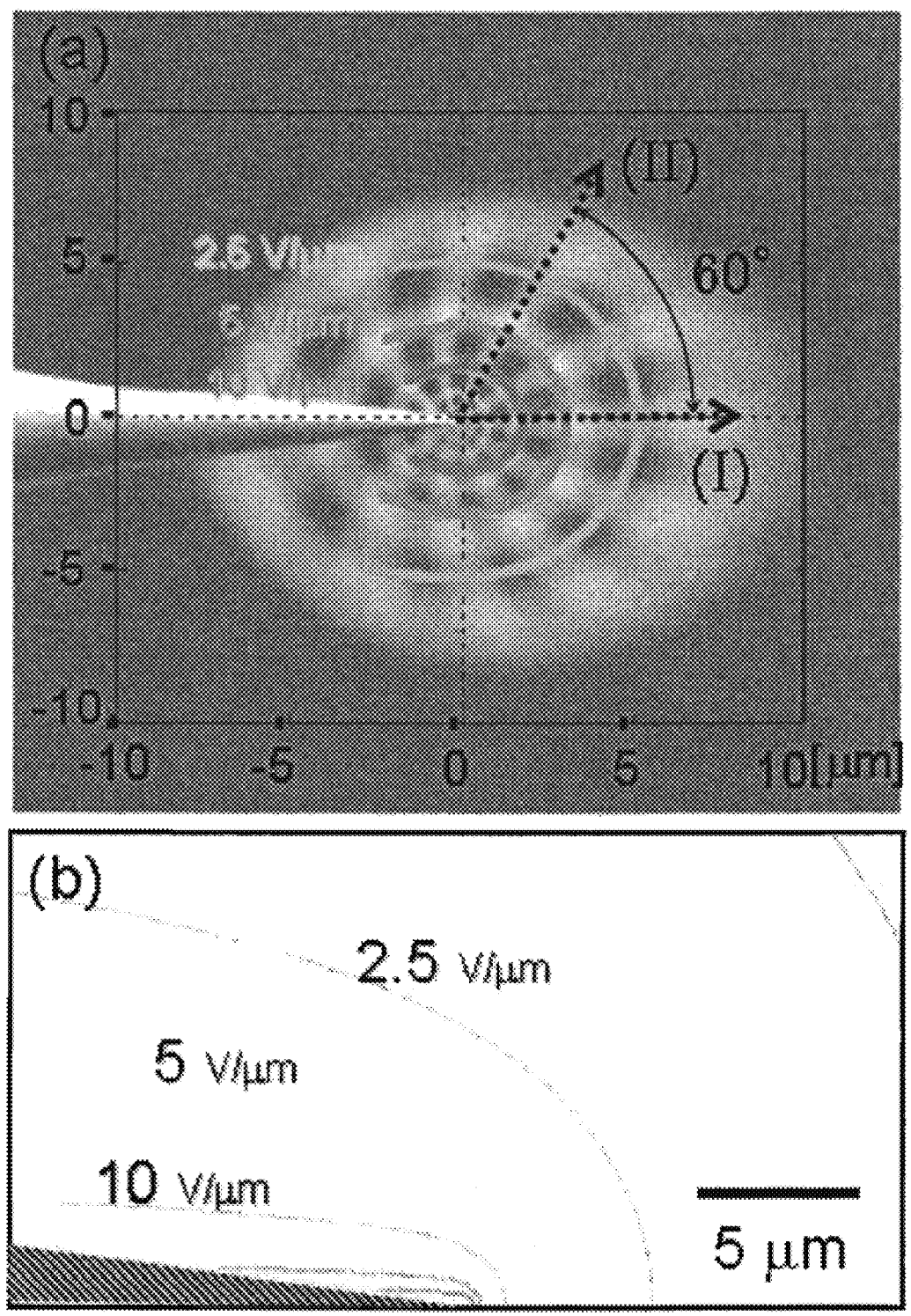
FIG. 9 is a view showing evaluation contours of 2.5V/μm, 5V/μm and 10V/μm and also is a view showing a result of simulation by a finite element method under corresponding conditions in the fourth embodiment of the present invention.

In this embodiment, as shown in FIG. 8(a), a plurality of grids 5 similar to the grids 5 shown in FIG. 1 and a plurality of grids 5 similar to the grids shown in FIG. 7 are arranged orthogonal to each other thus constituting a grid-like detection element. Here, FIG. 8(b) shows a visualized image when a bias voltage applied to the anode 8 is set to +205V and an acceleration voltage applied to the electronic line is set to 5 KeV (other conditions being substantially equal to corresponding conditions adopted by the first embodiment). Scanning positions A, B, C in FIG. 8(b) correspond to grid positions A', B', C' in FIG. 8. The relationship between both positions satisfies a scheme of Rutherford scattering. Due to such a constitution, two-dimensional mapping of the visualized image of the local electrode can be realized.

FIG. 9(a) shows evaluation contours of 2V/μm, 5V/μm, 5V/μm and 10V/μm, and FIG. 9(b) shows a result obtained by simulation using a finite element method under the same experimental conditions. It is understood that the result of the experiment favorably agrees with the result of simulation using a finite element method.

Figure 10:
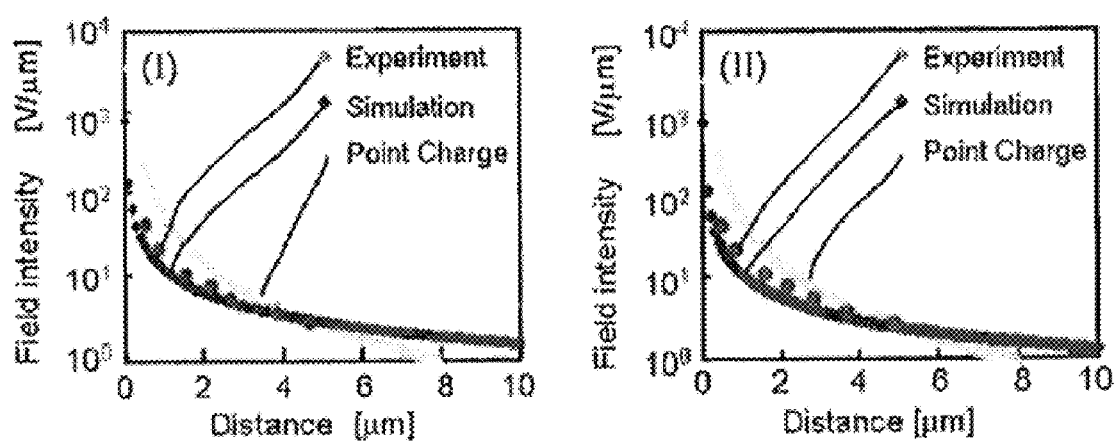
FIG. 10 is a graph showing a profile along a probe axis when a two-dimensional intensity profile is formed and a profile along a line inclined from the probe axis by 60° in the fourth embodiment of the present invention.
Figure 11:
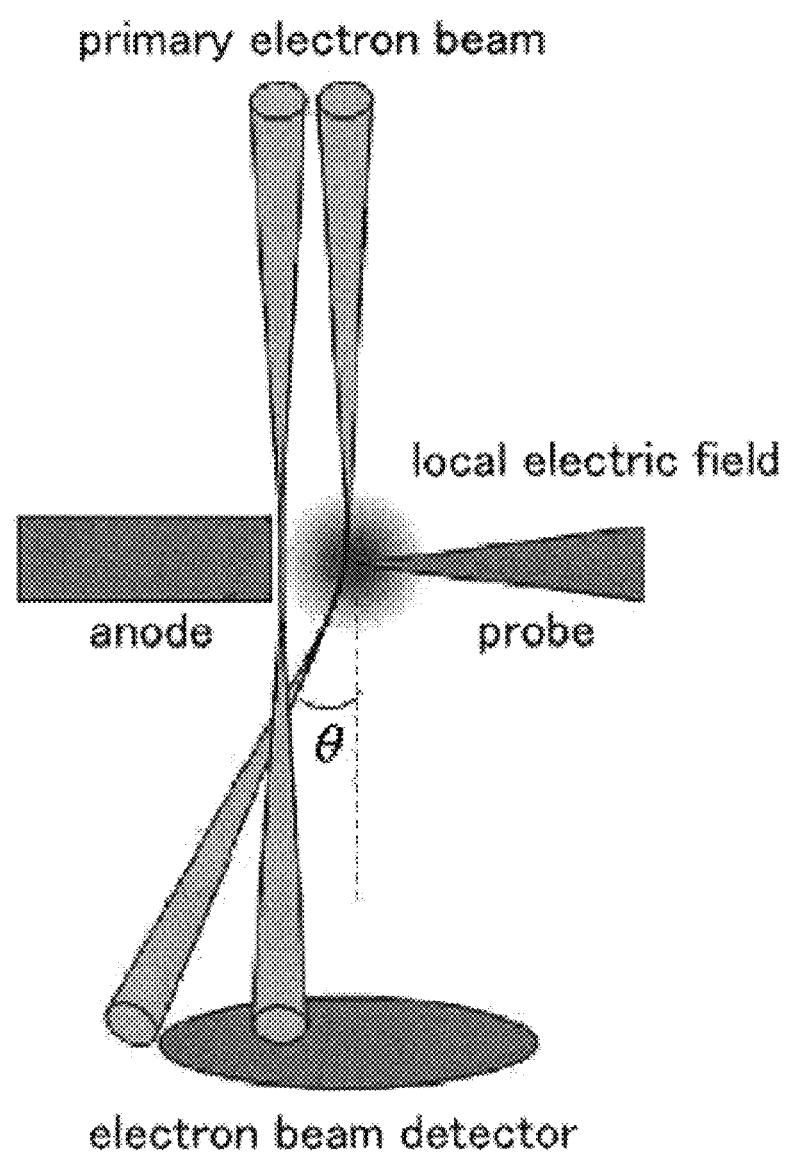
FIG. 11 is a schematic view showing a mode of deflection of an electron orbit by a local electric field.
Figure 12:
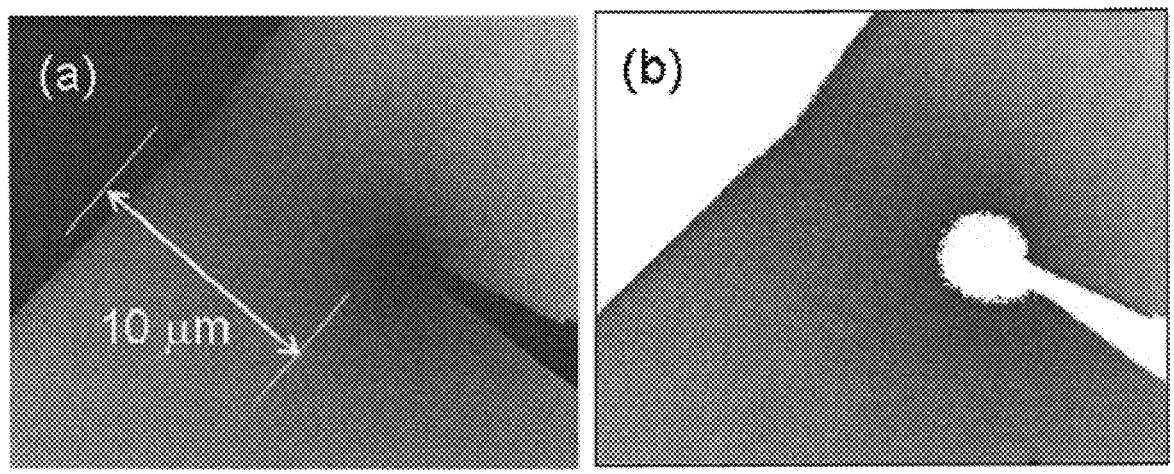
FIG. 12 is a schematic view showing the visualization of an electric field in a transmission scanning microscope.

FIG. 10 is a view showing plots when two-dimensional intensity profiles are constituted based on the scheme, wherein the profile (I) is formed of plots along a probe axis, the profile (II) is formed of plots along a line of 60° from the probe axis. The thin plots are the prediction made by point charge models, the intermediate thick plots show the result of the experiment, and the thickest plot indicates the result of simulation using an finite element method.

Due to such a constitution, the two-dimensional mapping of a local electric field can be realized.

Symbols in The Drawing Indicate The Following Part.
1 primary electron beam
2 conductive sample
2a projecting portion (tip end of probe or the like)
3 electron beam detector (STEM detector)
4 scattered and deflected primary electron beam
5 grid
6 secondary electron detector
7 silicon substrate (substrate for detection element)
8 anode
9 emitted secondary electrons
10 bias line
11 bias power source
12 voltage detector
13 shift register Industrial Applicability An application example of the present invention is a technique which visualizes a local electric field induced by a nano structural body in situ, and the present invention is applicable to a development and an analysis of a solid device, a CNT transistor, a light emitting or light absorbing element, an electron emitting element and the like. Further, the application of the present invention to a mechanical distortion analysis, an operation analysis and the like dependent on a local electric field of a nano structural body, MEMS and the like can be named.

The invention claimed is:

1. A method for visualizing the distribution of a local electric field formed near a sample in an electron beam scanning optical system, wherein a primary electron beam which passes through the local electric field formed near the sample is deflected by the local electric field, secondary electrons which are generated and emitted from a detection element provided downstream of an orbit of the deflected primary electron beam are detected by a secondary electron detector, and an image formed based on the detected signal and a scanning electron beam image obtained by scanning the sample are synthesized thus visualizing the distribution of the local electric field in multiple tone.

2. The method for visualizing the distribution of a local electric field according to claim 1, wherein the sample has a projecting portion, and the local electric field is formed near the projecting portion.

3. The method for visualizing the distribution of a local electric field according to claim 1, wherein a potential is applied to the sample.

4. The method for visualizing the distribution of a local electric field according to any one of claim 1, wherein a detection element having the grid structure which is constituted of a plurality of linear portions arranged in a spaced-apart manner at a fixed interval is used as the detection element.

5. The method for visualizing the distribution of a local electric field according to claim 4, wherein a detection element in which two sets of grid structures each of which is constituted of a plurality of linear portions are arranged orthogonal to each other is used as the detection element.

6. The method for visualizing the distribution of a local electric field according to claim 4, wherein a detection element in which a grid is formed on a substrate, the grid is constituted of a metal element, and a constitutional element of the grid and a constitutional element of the substrate differ from each other in secondary electron generation efficiency with respect to a bombardment of a primary electron beam is used as the detection element.

7. The method for visualizing the distribution of a local electric field according to claim 6, wherein the detection element in which the grid is constituted of Al, Cu or Au is used.

8. The method for visualizing the distribution of a local electric field according to claim 4, wherein a bias voltage is applied to the grid.

9. The method for visualizing the distribution of a local electric field according to claim 8, wherein a contrast of an image which indicates the distribution of the local electric field is adjusted by adjusting intensity of the bias voltage applied to the grid.

10. The method for visualizing the distribution of a local electric field according to claim 4, wherein grid lines which constitute the detection element are individually connected to an A/D converter means, and a scattering angle of the primary electron beam based on the local electric field is detected based on a signal from the A/D converter means.

11. A method for evaluating a local electric field distribution characteristic, wherein a distribution characteristic of a local electric field of the sample is evaluated using the method for visualizing the distribution of a local electric field described in claim 1.

12. The method for evaluating a local electric field distribution characteristic according to claim 11, wherein the dependency of a mechanical distortion or an operation of the sample on the local electric field is evaluated.

13. A local electric field distribution visualizing device for visualizing the distribution of a local electric field formed near a sample in an electron beam scanning optical system in multiple tone, the local electric field distribution visualizing device comprising at least:

(a) a scanning radiation part which irradiates a primary electron beam to the sample; (b) a detection part which detects the primary electron beam; (c) a detection element part which detects the primary electron beam deflected by a local electric field formed on the sample; (d) a secondary electron detection part which detects secondary electrons generated and emitted from the detection part which detects the primary electron beam; (e) an image conversion part which converts a signal from the secondary electron detection part; (f) an image conversion part which converts a signal from the primary electron beam detection part; and (g) an image synthesizing and displaying part which synthesizes and displays images from the image conversion parts (e), (f).

14. The local electric field distribution visualizing device according to claim 13, wherein the sample has a projecting portion, and the local electric field is formed near the projecting portion.

15. The local electric field distribution visualizing device according to claim 13, wherein a potential applying part which applies a potential to the sample is provided.

16. The local electric field distribution visualizing device according to claim 13, wherein the detection element part (c) includes a detection element having the grid structure which is constituted of a plurality of linear portions arranged in a spaced apart manner at a fixed interval.

17. The local electric field distribution visualizing device according to claim 16, wherein the detection element part (c) includes a detection element in which two sets of grid structures each of which is constituted of a plurality of linear portions are arranged orthogonal to each other.

18. The local electric field distribution visualizing device according to claim 16, wherein the device includes a grid bias voltage applying part which applies a bias voltage to the grid.

* * * * *